Figure 1:
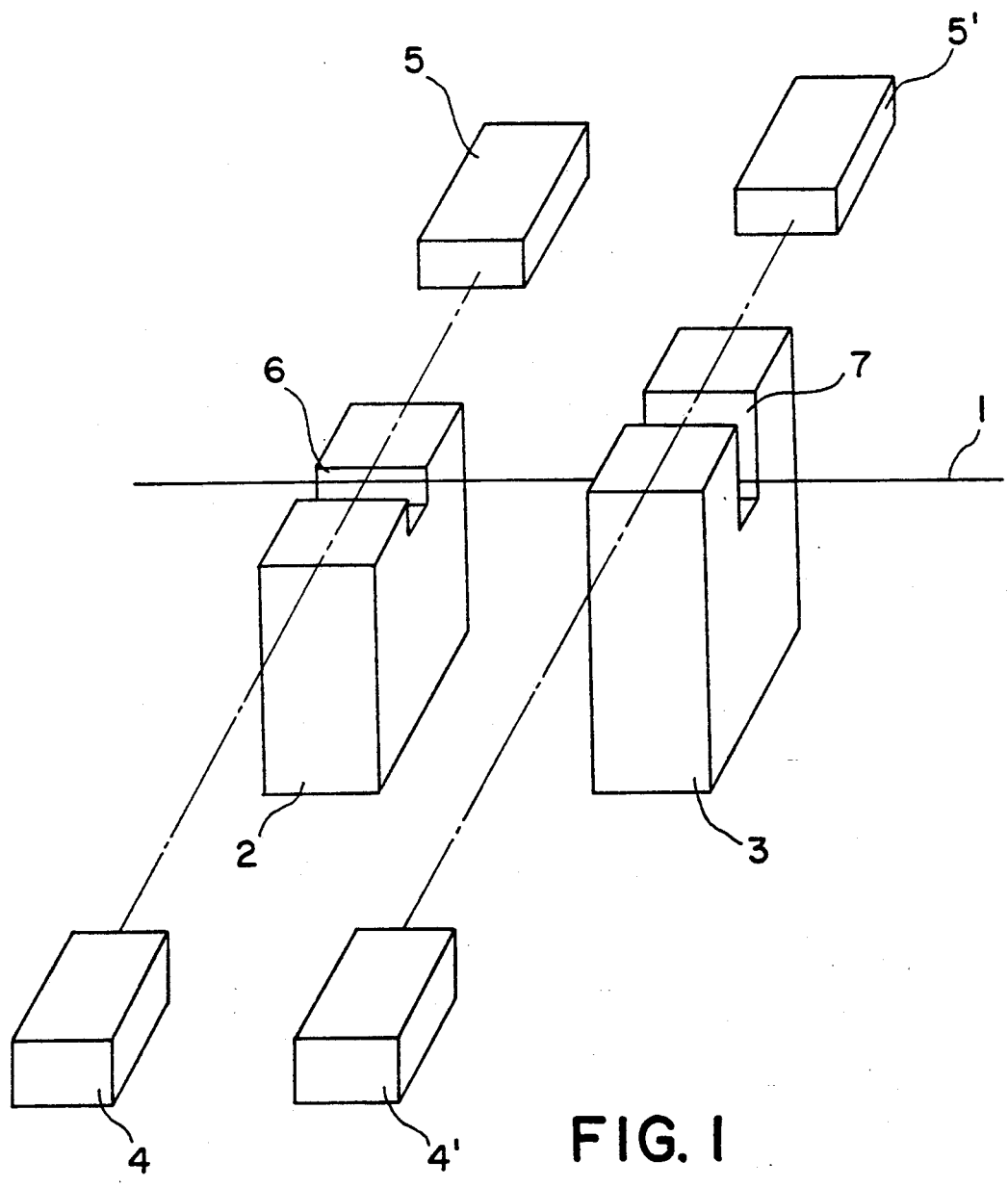

United States Patent
Hagmann

Patent Number: 5,182,457
Date of Patent: Jan. 26, 1993

[54] DEVICE FOR PHOTO-ELECTRICALLY MONITORING A MOVING YARN USING TWO SENSOR HEADS

[75] Inventor: Karl Hagmann, Emmenbrücke, Switzerland

[73] Assignee: Rhone-Poulenc Viscosuisse SA, Emmenbrucke, Switzerland

[21] Appl. No.: 752,638

[22] PCT Filed: Jan. 7, 1991

[86] PCT No.: PCT/CH91/00003
§ 371 Date: Aug. 26, 1991
§ 102(e) Date: Aug. 26, 1991

[87] PCT Pub. No.: WO91/10898
PCT Pub. Date: Jul. 25, 1991

[30] Foreign Application Priority Data
Jan. 12, 1990 [CH] Switzerland ............ 102/90

[51] Int. Cl.$^5$ ............................ G01N 21/88
[52] U.S. Cl. ..................... 250/572; 356/430
[58] Field of Search .......... 250/572, 562, 561, 571; 57/264; 356/430, 238

[56] References Cited

U.S. PATENT DOCUMENTS

| | | | |
|---|---|---|---|
| 3,907,440 | 9/1975 | Eichenberger et al. | 356/238 |
| 4,716,942 | 1/1988 | Jensen et al. | 250/571 |
| 4,743,749 | 5/1988 | Grundyu . | |
| 4,963,757 | 10/1990 | Vanliefde et al. . | |
| 4,970,402 | 11/1990 | Devuyst et al. . | |
| 5,036,568 | 8/1991 | Goineau | 57/264 |

Primary Examiner—Edward P. Westin
Assistant Examiner—K. Shami
Attorney, Agent, or Firm—Seidel, Gonda, Lavorgna & Monaco

[57] ABSTRACT

A device to monitor a moving yarn for irregularities is described. A first sensor head (2) with a recess (6) and a second sensor head (3) with a recess (7) are arranged in the direction of yarn movement. The cross-sectional depth of the recess (7) in second sensor head (3) is deeper than that of the recess (6) of sensor head (2). It is therefore possible, for example, to record separately slubs and projecting fibers. The monitoring device can be automated and used for quality control of any type of yarn.

6 Claims, 2 Drawing Sheets

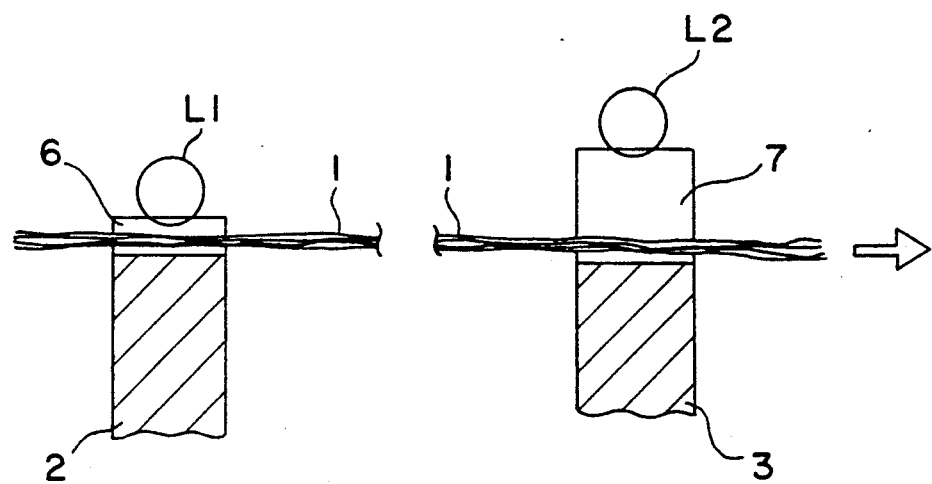
FIG. 2a  FIG. 2b
FIG. 3
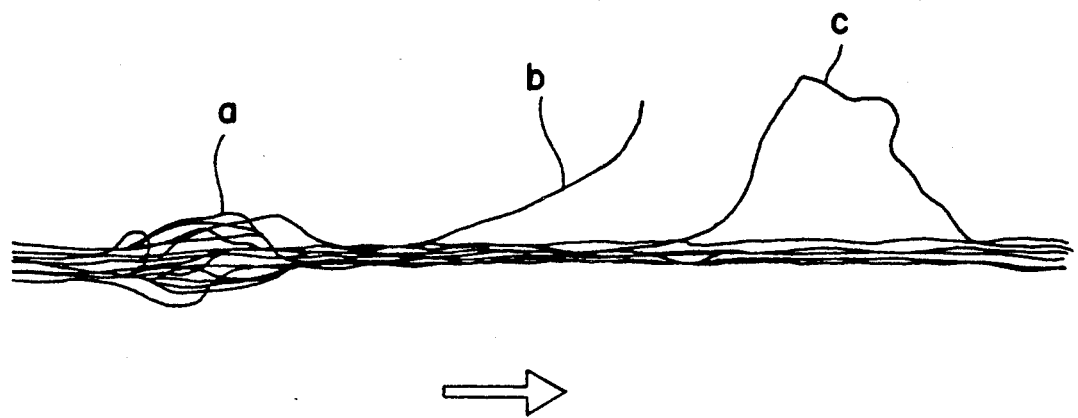

DEVICE FOR PHOTO-ELECTRICALLY MONITORING A MOVING YARN USING TWO SENSOR HEADS

The invention involves a device for photo-electrically monitoring a moving yarn for irregularities, consisting of sensor heads connected in series in the direction of yarn movement, where both the first and second sensor heads are attached to a beam transmitter and a beam receiver.

It is known that different irregularities can have different effects on individual yarn during further processing or as the finished product. Slubs, for example, generally cause defects in further processing. A specific small number of projecting fibres, for example, could be tolerated for certain final uses of yarn. For this reason it would be beneficial if every defect could be recorded individually for an assessment of quality.

The photo-electric monitoring of a moving yarn is already known U.S. Pat. No. 729,635). Here a silhouette of the yarn group is converted into an electric signal, which nullifies the values existing below a cut-off limit and when there are values above the cut-off limit shuts off the textile machine. Further development has led to a continual increase in sensitivity. Yet, even with increased sensitivity small yarn defects could not be recorded because of the background noise. A yarn consists generally of individual fibers and, because of its surface, never displays a completely homogeneous, rounded cross-section. Twisting movements, uneven yarn movement and a not entirely level yarn thus produces a broader, more diffuse silhouette during the overshadowing then the actual yarn cross-section shows. This diffuse section of the silhouette is described as the basic noise of the moving yarn. Small defects are lost in this basic noise level. In practice this basic noise varies in value between 10 and 120% of the yarn cross-section.

No indications about the direction of the yarn and measurement of its irregularities are evident in the publication. Using all known devices and methods individual types of defects cannot be differentiated.

The objective of the invention is to make available a device to control a moving individual yarn, which differentiates irregularities recorded by type of defect, especially so-called slubs, or projecting fibres and/or thin or thick areas in monofilaments.

The invention achieved this by equipping both the first and second sensor heads with recesses, in which the cross sectional depth of the second sensor head recess is larger than the first sensor head recess.

On the first sensor head, sensitivity can be adjusted variably. Since the yarn is only slightly lowered into the recess, only major yarn irregularities, e.g. slubs, are detected by the first sensor head when it is set at high sensitivity. The second sensor head detects all occurrences, i.e., even broken fibers, which protrude above the upper edge of the recess. The yarn is, dependent on the level of detection, lowered into the recess of the second sensor head, so that various types of defects and irregularities in the yarn can be determined simultaneously in one pass.

No known method is as yet able to use exclusively the shadow cast by the moving yarn's projecting defects for signal evaluation and thus also for differentiation of defects.

Automatic distinguishing of various defects creates sorting possibilities and thus introduces certain advantages with regard to quality control of a yarn. Automatic controls are labor saving with regard to monitoring and the determination of defects, as well as providing an immediate assessment of the current production's actual quality.

There are various cross-sectional profiles, as, for example, V-shaped or rectangular cross-sections are suitable for gauging. Particularly advantageous in the cross-sectional depth of the second sensor head which is at least 1.02 times, in particular 2 -5 times, preferably 1.5-3 times deeper than the cross-sectional depth of the first sensor head. The width of the slot should be at least as large as the yarn cross-section, in particular 1.1-10 times, preferably 1.5-2 times larger. Using the invented device even thick areas in monofilaments can be determined and sorted simply.

It is advisable that the recesses be interchangeable optional units. Thus it is possible to detect an entire spectrum of deniers with a basic unit in combination with various optional pieces. In practice deniers in the range of 0.5 up to 10,000 dtex, preferably 5 up to 3,000 dtex, can be monitored by the invented device.

The invention will be described in more greater with the aid of a diagram. It shows:

FIG. 3 a schematic arrangement of the invention's monitoring and measuring device.

FIG. 2a a slot through the first sensor head in the area of yarn movement

FIG. 2b a slot through the second sensor head in the area of yarn movement

FIG. 3a a slub (yarn defect, thick spot)

FIG. b a broken fiber (individual thread)

FIG. c a projecting fiber (loop)

In FIG. 1 the moving yarn is designated 1. The yarn can be a multifilament, monofilament or a fiber yarn. Aligned with a first sensor head 2 are a beam transmitter 4 and a beam receiver 5; a second sensor head 3 is aligned with a beam transmitter 4 and a beam receiver 5. The sensor head 2 is equipped with a recess 6, and the sensor head 3 is equipped with a recess 7. The recess 7 can be in the form of an eccentric cam or a wedge or some other adjustable means.

In FIG. 2a a light beam L1 from beam transmitter 4 is directed to sensor head 2. The shallow depth of the recess 6 shows that a yarn 1 is only slightly down in it. Here, only large yarn defects e.g. slubs (FIG. 3a), not individual fibers (FIG. 3b), are detected.

In FIG. 2b a light beam L2 from beam transmitter 4 is directed at the sensor head 3. Here, the yarn 1 is down deep in the recess 7 of sensor head 3. All phenomena in individual fibers, which protrude above the edge A, are detected.

The depth to which the yarn 1 is down depends on the desired degree of detection.

In FIG. 3 slubs are designated a), projecting broken fibres are designated b) and projecting loops designated c). The advantage of the invention lies in the accurate detection and automatic registration of irregularities in a moving yarn, in which the individual occurrences are also detected according to their type. The invention is particularly suitable for controlling the monitoring of quality in an individual yarn.

In place of only two, several sensor heads arranged in series with successively variable sensitivity could be introduced to grade the various sortings. The invention's monitoring means can also be combined with an integrated broken yarn monitor. It can be particularly advantageous when housed in a grounded, enclosed, compact casing. False readings, caused by example by uneven yarn movement, could be essentially reduced by means of a verification circuit.

I claim:

1. A device for photo-electrically monitoring a moving yarn (1) for irregularities, consisting of sensor heads connected in series in the direction of yarn movement, in which a beam transmitter (4) and a beam receiver (5) are aligned with a first sensor head (2) and a beam transmitter (4') and a beam receiver (5') are aligned with a second sensor head (3), thereby characterized in that the first sensor head (2) is equipped with a recess (6) and the second sensor head is equipped with a recess (7), where the cross-sectional depth of the recess (7) of the second sensor head (3) is greater than the recess (6) of the first sensor head (2).

2. A device according to claim 1, thereby characterized in that the cross-sectional depth of the recess (7) is at least 2.0% greater than the cross-sectional depth of the recess (6).

3. A device according to claim 1, wherein the cross sectional profile of the recesses are V-shaped.

4. A device according to claim 1, wherein the cross sectional profile of the recesses are right-angled.

5. A device according to claim 1, thereby characterized in that the recesses (6,7) are interchangeable optional units 6. A device according to claim 1 wherein the recess (6) through the first sensor head is 1.1 to 10 times wider than the cross section of the yarn.

* * * * *